US00PP32602P2

(12) United States Plant Patent
Hartman

(10) Patent No.: US PP32,602 P2
(45) Date of Patent: Dec. 8, 2020

(54) ***CALADIUM* PLANT NAMED 'JPD OF14-457'**

(50) Latin Name: ***Caladium* X *hortulanum***
Varietal Denomination: JPD OF14-457

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/873,503

(22) Filed: Apr. 23, 2020

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'JPD OF14-457', characterized by its compact, intermediate height and somewhat mounding plant habit; dense and bushy appearance; moderately vigorous growth habit and moderate growth rate; fancy-type leaves that are dark green in color with dark red-colored centers and venation; and petioles that are tan in color flushed with reddish purple.

5 Drawing Sheets

Figure 1:
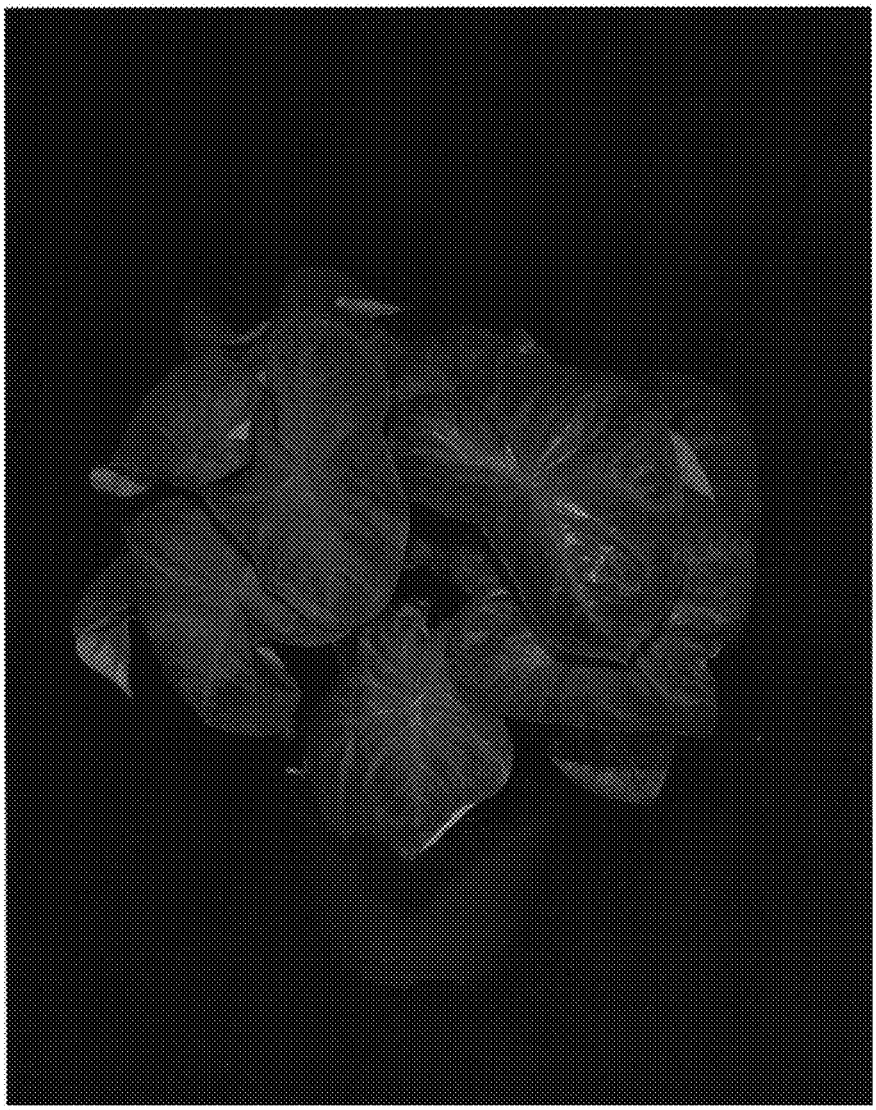

Botanical designation: *Caladium* X *hortulanum*.
Cultivar denomination: 'RD OF14-457'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'RD OF14-457'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2013 in Avon Park, Fla. of *Caladium* X *hortulanum* 'BRZ Rd Fcy 07', a non-patented proprietary cultivar typically used for breeding purposes, as the female, or seed, parent with *Caladium* X *hortulanum* 'RD 153-20', disclosed in U.S. Plant Pat. No. 27,944, as the male, or pollen, parent. The new *Caladium* plant was discovered and selected by the Inventor as a single plant within the progeny of the stated cross-pollination in a controlled outdoor nursery environment in Avon Park, Fla. in September, 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RD OF14-457'. These characteristics in combination distinguish 'RD OF14-457' as a new and distinct *Caladium* plant:

1. Compact, intermediate in height and somewhat mounding plant habit; dense and bushy appearance.
2. Moderately vigorous growth habit and moderate growth rate.
3. Fancy-type leaves that are dark green in color with dark red-colored centers and venation.
4. Petioles that are tan in color flushed with reddish purple.

Plants of the new *Caladium* differ primarily from plants of the female parent, 'BRZ Rd Fcy 07', in the following characteristics:

1. Plants of the new *Caladium* are more compact and mounded than and not as tall and upright as plants of 'BRZ Rd Fcy 07'.
2. Leaves of plants of the new *Caladium* are more rugose than leaves of plants of 'BRZ Rd Fcy 07'.
3. Plants of the new *Caladium* and 'BRZ Rd Fcy 07' differ in leaf color as leaves of the new *Caladium* are dark green in color with dark red-colored centers and venation whereas leaves of 'BRZ Rd Fcy 07' are reddish bronze in color with red-colored centers and venation.
4. Plants of the new *Caladium* and 'BRZ Rd Fcy 07' differ in leaf petiole color as leaf petioles of the new *Caladium* are tan in color flushed with reddish purple whereas leaf petioles of 'BRZ Rd Fcy 07' are close to black in color.

Plants of the new *Caladium* differ primarily from plants of the male parent, 'JPD 153-20', in the following characteristics:

1. Plants of the new *Caladium* are intermediate in height whereas plants of 'ND 153-20' are short to intermediate in height.
2. Plants of the new *Caladium* grow faster than plants of 'JPD 153-20'.
3. Leaves of plants of the new *Caladium* are more rugose than leaves of plants of 'JPD 153-20'.
4. Plants of the new *Caladium* and 'JPD 153-20' differ in leaf color as leaves of the new *Caladium* are dark green in color with dark red-colored centers and venation whereas leaves of 'JPD 153-20' are bright red in color with dark green-colored margins.
5. Plants of the new *Caladium* and 'JPD 153-20' differ in leaf petiole color as leaf petioles of the new *Caladium* are tan in color flushed with reddish purple whereas leaf petioles of 'JPD 153-20' are deep red in color.

Plants of the new *Caladium* can be compared to plants of *Caladium* X *hortulanum* 'John Peed', not patented. In side-by-side comparisons, plants of the new *Caladium* differ primarily from plants of 'John Peed' in the following characteristics:

1. Plants of the new *Caladium* are shorter than and more mounding than plants of 'John Peed'.
2. Leaves of plants of the new *Caladium* are more rugose than leaves of plants of 'John Peed'.
3. Plants of the new *Caladium* and 'John Peed' differ in leaf color as leaves of the new *Caladium* are dark green in color with dark red-colored centers and venation whereas leaves of 'John Peed' have red-colored centers with olive green-colored margins.

Plants of the new *Caladium* can also be compared to plants of *Caladium* X *hortulanum* 'Frieda Hemple', not patented. In side-by-side comparisons, plants of the new *Caladium* differ primarily from plants of 'Frieda Hemple' in the following characteristics:

1. Plants of the new *Caladium* and 'Frieda Hemple' differ in leaf color as leaves of the new *Caladium* are dark green in color with dark red-colored centers and venation whereas leaves of 'Frieda Hemple' are medium green in color with bright red-colored centers and venation.
2. Leaves of plants of the new *Caladium* are more rugose than leaves of plants of 'Frieda Hemple'.
3. Plants of the new *Caladium* and 'Frieda Hemple' differ in leaf petiole color as leaf petioles of the new *Caladium* are tan in color flushed with reddish purple whereas leaf petioles of 'Frieda Hemple' are close to black in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 6) is a side perspective view of a typical plant of 'JPD OF14-457' in a container and grown in a shade house (tuber de-eyed).

Figure 2:
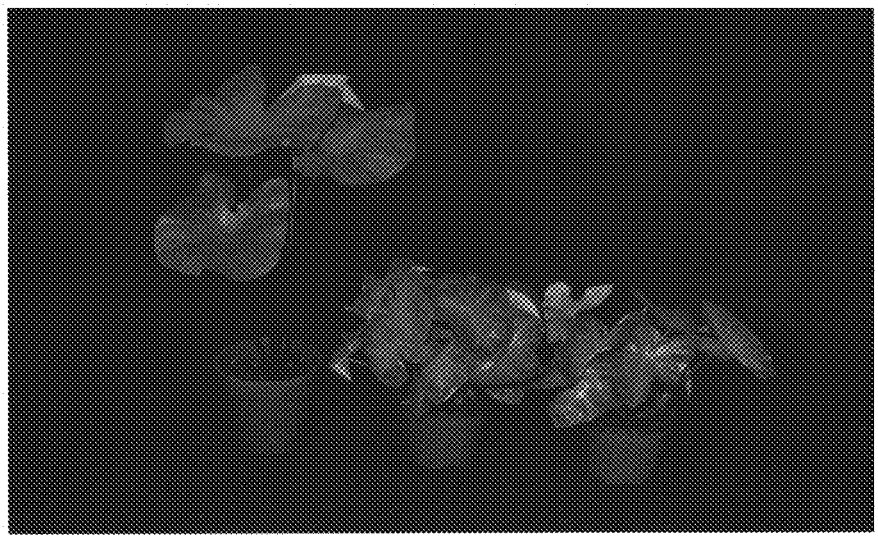

The photograph at the top of the second sheet (FIG. 2 of 6) is a comparison view of typical potted plants of the female parent, 'BRZ Rd Fcy 07' (left), 'JPD OF14-457' (center) and the male parent, 'JPD 153-20' (right).

Figure 3:
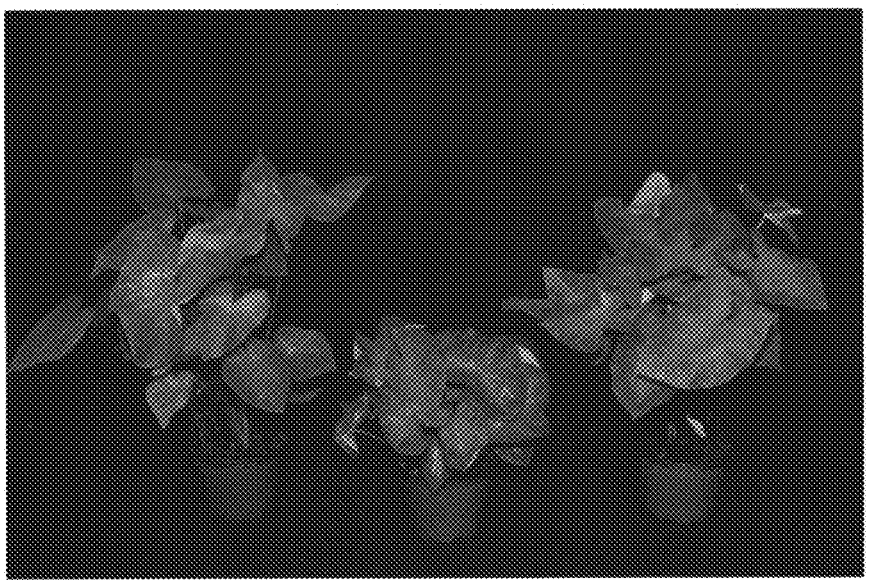

The photograph at the bottom of the second sheet (FIG. 3 of 6) is a comparison view of typical potted plants of 'John Peed' (left), 'JPD OF14-457' (center) and 'Frieda Hemple' (right).

Figure 4:
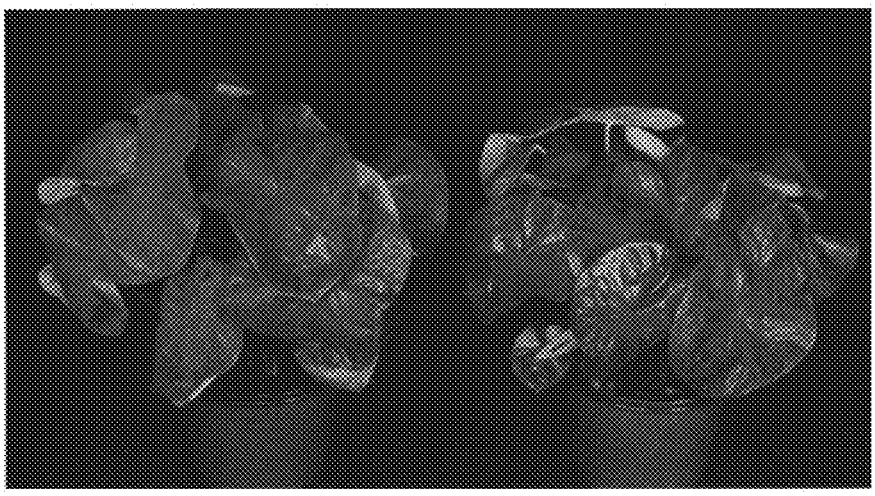

The photograph on the third sheet (FIG. 4 of 6) is a comparison view of typical plants of 'JPD OF14-457' grown in containers, the plant on the left has not had its tuber de-eyed and the plant on the right has had its tuber de-eyed prior to planting.

Figure 5:
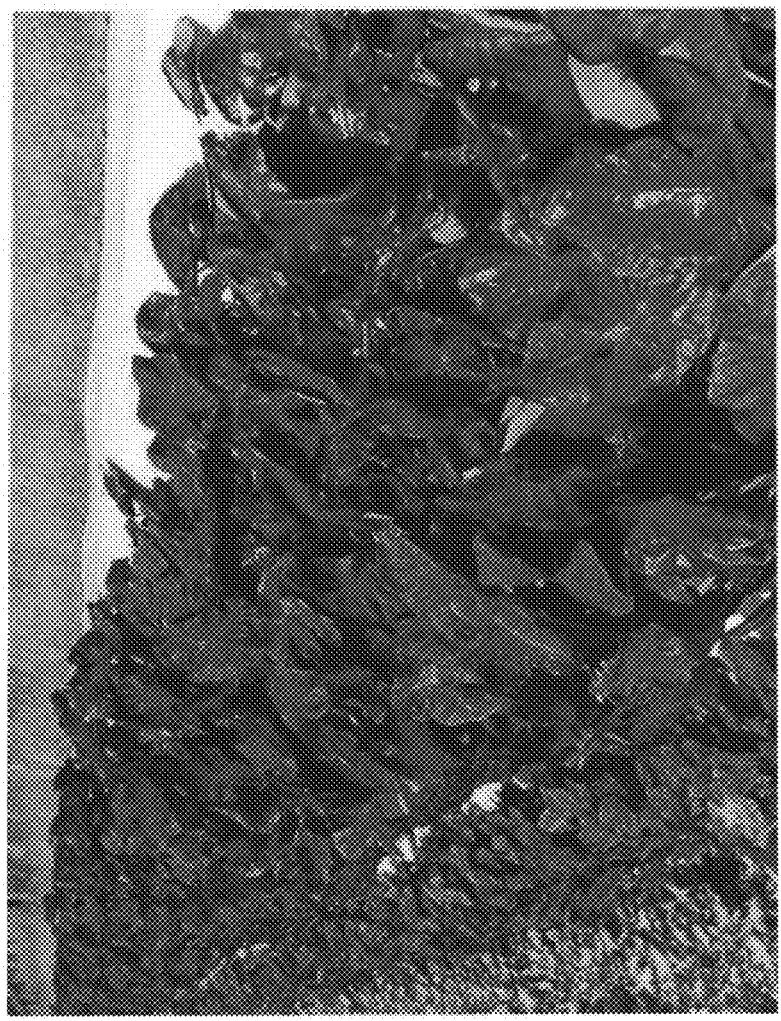

The photograph on the fourth sheet (FIG. 5 of 6) is a side perspective view of typical plants of 'JPD OF14-457' grown in an open production field.

Figure 6:
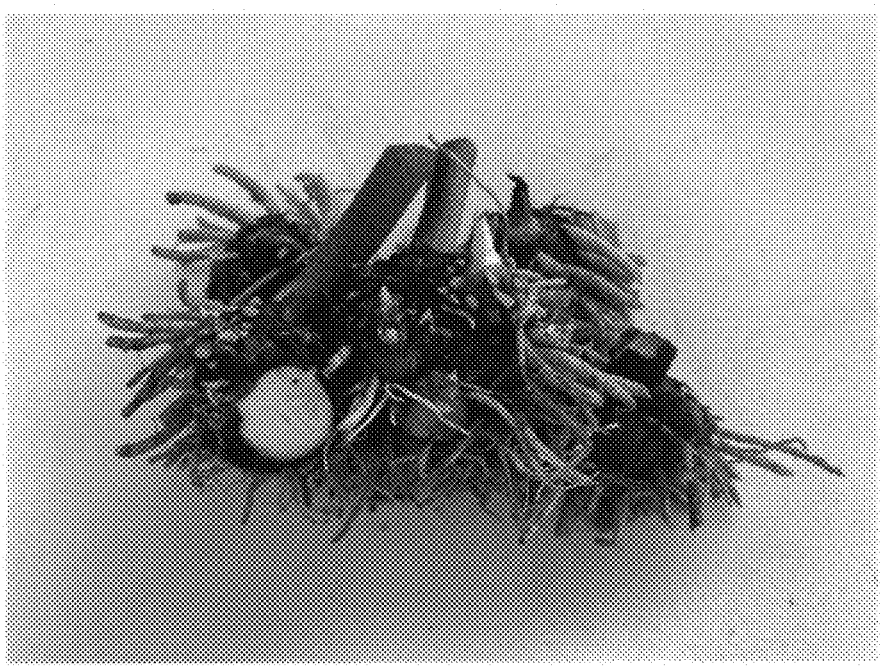

The photograph on the fifth sheet (FIG. 6 of 6) is a close-up view of typical freshly-harvested tubers with roots and leaf petioles of 'JPD OF14-457'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were seven weeks old and plants grown in the outdoor nursery were 28 weeks old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'JPD OF14-457'.

Parentage:

*Female, or seed, parent.*—*Caladium* X *hortulanum* 'BRZ Rd Fcy 07', not patented, proprietary cultivar typically used for breeding.

*Male, or pollen, parent.*—*Caladium* X *hortulanum* 'JPD 153-20', disclosed in U.S. Plant Pat. No. 27,944.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments mostly round or ovate in shape. Height: About 4.2 cm. Diameter: About 8.3 cm to 10.6 cm. Segment height: About 2.7 cm. Segment diameter: About 3.1 cm. Axillary bud shape: Roughly triangular. Axillary bud size: About 4 mm by 6 mm. Texture: Thick, starchy; somewhat brittle. Color: Periderm, freshly-harvested: Close to 177B to 177C and N199C. Periderm, dried: Close to 200A. Epidermis: Initially, close to 173D becoming closer to 161C to 161D with development. Cortical tissue: Close to 2D and 4D. Axillary buds: Close to 174D and 179D. Root description: Thick, fleshy contractile roots with few lateral branches; color, close to NN155D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Compact, intermediate in height and somewhat mounding plant habit; dense and bushy appearance; moderately vigorous growth habit and moderate growth rate; potted plants finish in saleable form in about six to seven weeks after planting tubers; leaf petioles and leaves arise from one or more growing points on tubers; leaf petioles initially upright and leaning outwardly with development.

*Plant height, from soil level to top of foliar plane, shade house-grown potted plants*.—About 24 cm to 34 cm.

*Plant diameter or spread, shade house-grown potted plants*.—About 36 cm to 42 cm.

*Number of shoots per plant, shade house-grown potted plants, tubers not de-eyed*.—About four to seven develop per #1 tuber.

*Number of shoots per plant, shade house-grown potted plants, tubers de-eyed*.—About four to eight develop per #1 tuber.

*Cataphylls, shade house-grown potted plants*.—Length: About 4.5 cm to 5 cm. Width: About 2 cm. Shape: Linear to wedge-shaped. Apex: Acute. Base: Sheathing the stem. Color: Outer surface: Close to 156C to 156D with stippling, streaks and tessellations, close to N199A to N199B and 199A; color becoming closer to N199B and 199A with development.

Leaf description:

*Arrangement and type*.—Alternate; simple; fancy-type.

*Length, shade house-grown potted plants*.—About 13.5 cm to 18.5 cm.

*Width, shade house-grown potted plants*.—About 11.2 cm to 13 cm; when flattened, about 11.5 cm to 14 cm.

*Shape*.—Broadly ovate, roughly cordate.

*Apex*.—Acute, cuspidate to obtuse.

*Base*.—Sagittate-peltate, cordate.

*Margin*.—Entire with broad undulations.

*Texture and luster, upper surface*.—Rugose, glabrous; initially glossy becoming matte with development.

*Texture and luster, lower surface*.—Rugose, glabrous; slightly glaucous; matte.

*Venation pattern*.—Pinnate.

*Color, shade house-grown potted plants*.—Developing and fully developed leaves, upper surface: Background color: Close to 137A and NN137A. Towards the margins: Close to 137A and NN137A. Leaf edge: Narrow, close to 183A, 187A and 187B. Basal notch: Close to 187A. Leaf attachment point: Close to 187A. Midvein: Close to 53A and 53B. Lateral venation: Close to 53A tinged with close to N186D. Interveinal areas and areas surrounding venation: Close to 53A, lighter than 53A and close to 53A tinged with close to 183B. Developing and fully developed leaves, lower surface: Background color: Close to 191A. Towards the margins: Close to 191A. Leaf edge: Close to 183A and 187A to 187B. Basal notch: Close to 53A. Leaf attachment point: Close to 53A. Midvein: Close to 53A tinged with close to 59B. Lateral venation: Close to 53A tinged with close to 59B. Interveinal areas: Close to 191A, 157B, 184A and 185B.

*Petioles*.—Aspect: Initially upright and straight and leaning outwardly with development; flexible. Length, shade house-grown potted plants: About 21.5 cm to 28.2 cm. Diameter, distally, shade house-grown potted plants: About 4 mm to 5 mm. Diameter, proximally, shade house-grown potted plants: About 6 mm to 9 mm. Texture and luster: Smooth, glabrous; slightly glaucous. Color, shade house-grown potted plants: When developing and fully developed: Close to N170D flushed with close to 181C and 177A and with variable and faint stippling, streaks and tessellations of close to 182B and 177D; just below the leaf junction, close to 60A tinged with close to 53B. Wing length, shade house-grown potted plants: About 5.1 cm to 7 cm. Wing diameter, shade house-grown potted plants: About 9.5 mm to 11 mm. Texture and luster, inner and outer surfaces: Smooth, glabrous; dull. Wing color, shade house-grown potted plants: Outer surface: Close to 156C to 156D with stippling, streaks and tessellations of close to N199A to N199B and 199A. Inner surface: Close to N155C and N155B; colors and patterns on the outer surface are visible on the inner surface.

Inflorescence description: To date, inflorescence development has not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'JPD OF14-457' as illustrated and described.

* * * * *